United States Patent [19]

Nohda

[11] Patent Number: 4,529,280
[45] Date of Patent: Jul. 16, 1985

[54] APPARATUS FOR SUBJECTIVELY MEASURING THE REFRACTIVE POWER OF AN EYE

[75] Inventor: Masao Nohda, Yokosuka, Japan

[73] Assignee: Nippon Kogaku K. K., Japan

[21] Appl. No.: 383,288

[22] Filed: May 28, 1982

[30] Foreign Application Priority Data

Jun. 4, 1981 [JP] Japan .................................. 56-84984

[51] Int. Cl.³ ............................ A61B 3/14; A61B 3/10
[52] U.S. Cl. ..................................... 351/211; 351/214
[58] Field of Search ......................... 351/211, 214, 205

[56] References Cited

U.S. PATENT DOCUMENTS 4,162,828 7/1979 Trachtman .......................... 351/211
4,353,625 10/1982 Nohda .................................. 351/211

Primary Examiner—Rodney B. Bovernick
Attorney, Agent, or Firm—Shapiro and Shapiro

[57] ABSTRACT

An apparatus for subjectively measuring the refractive power of an eye includes obliquely disposed beam splitter means, diaphragm means provided on the reflection optical axis of the beam splitter means and having a pair of openings symmetric with the reflection optical axis, collimation mark means provided on the reflection optical axis of the beam splitter means and on the side opposite to the beam splitter means, first imaging lens means provided between the beam splitter means and the diaphragm means, second imaging lens means provided between the diaphragm means and the collimation mark means, rotating means for rotating an image of the openings of the diaphragm means about the reflection optical axis, means for varying the optical distance of the collimation mark means relative to the diaphragm means, first converter means for causing the angle of rotation of the rotating means to correspond to the direction of the astigmatism axis, and second converter means for causing the optical distance between the diaphragm means and the collimation mark means to correspond to the refractive power.

13 Claims, 9 Drawing Figures

APPARATUS FOR SUBJECTIVELY MEASURING THE REFRACTIVE POWER OF AN EYE

BACKGROUND OF THE INVENTION

1. Field of the Invention

This invention relates to an apparatus for subjectively measuring the refractive power of an eye.

2. Description of the Prior Art

The method of measuring the refractive power of the eye is grouped into the subjective examination and objective examination. Generally, however, objective examination is carried out to obtain the aim of the refractive power of the eye and finally, the refractive power of the eye is determined by the subjective examination.

In the conventional subjective examination, the refractive power of the eye has usually been determined with visual acuity as the standard. That is, a visual acuity measurement has been carried out by the use of a visual acuity examination mark and the refractive power of the eye has been determined with the measured visual acuity as the standard. In some cases, it has been difficult to judge from which visual acuity the refractive power of the eye should be obtained. This is because it cannot always be said that the best visual acuity is the best refractive power. This is known as the problem of over-rectification. Also, the visual acuity measurement itself has been carried out by comparing objects before and after in terms of time, and therefore, it has been very difficult for the examinee to judge which of the objects before and after can be seen better, causing fatigue of the examinee.

SUMMARY OF THE INVENTION

It is a first object of the present invention to provide an apparatus for subjectively measuring the refractive power of an eye which can measure the refractive power of the eye to be examined independently of the visual acuity of the eye and which forces no difficult judgments upon the examinee during measurement.

It is a second object of the present invention to provide an apparatus for measuring the refractive power of an eye which can measure the refractive power of the eye simply by the examinee judging whether two images have become coincident with each other.

The invention will become more fully apparent from the following detailed description of an embodiment thereof taken in conjunction with the accompanying drawings.

DESCRIPTION OF THE PREFERRED EMBODIMENT

Figure 1:
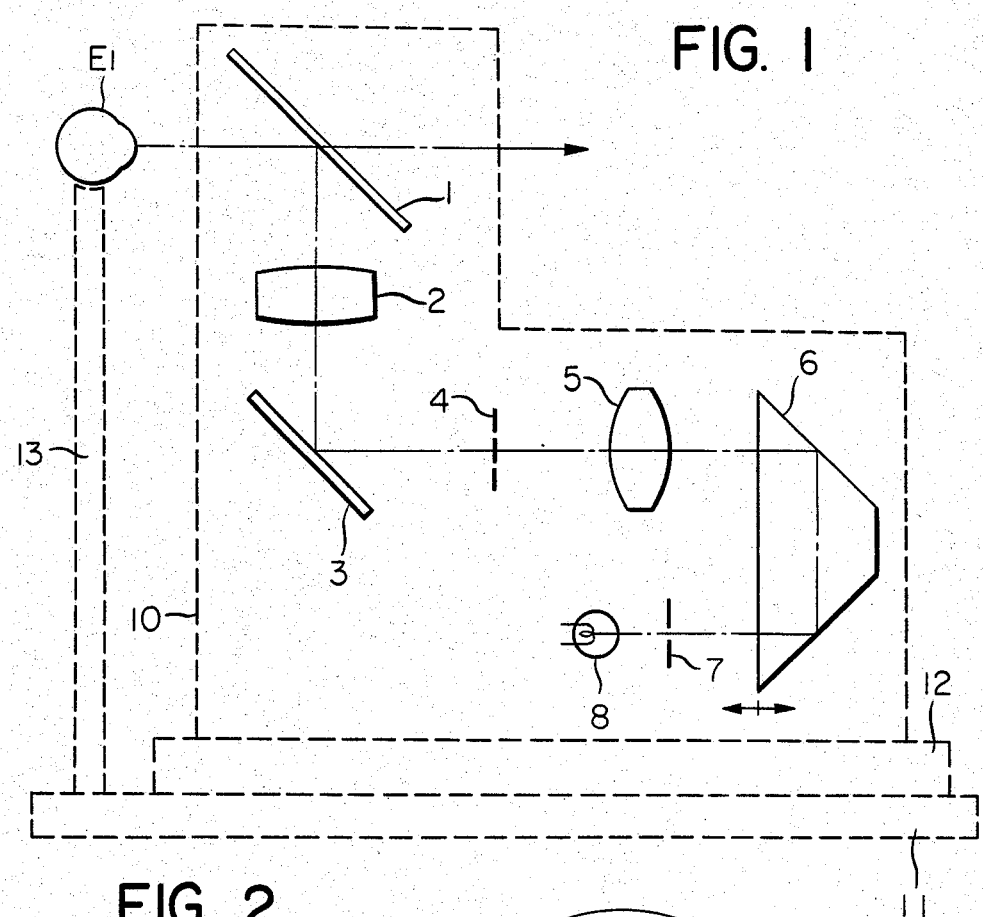
FIG. 1 shows the construction of an embodiment of the present invention.

FIG. 1 shows the optical system of an embodiment of the present invention. The optical system has an optical path extending from $E_1$ to 8, as explained hereinafter.

Figure 2:
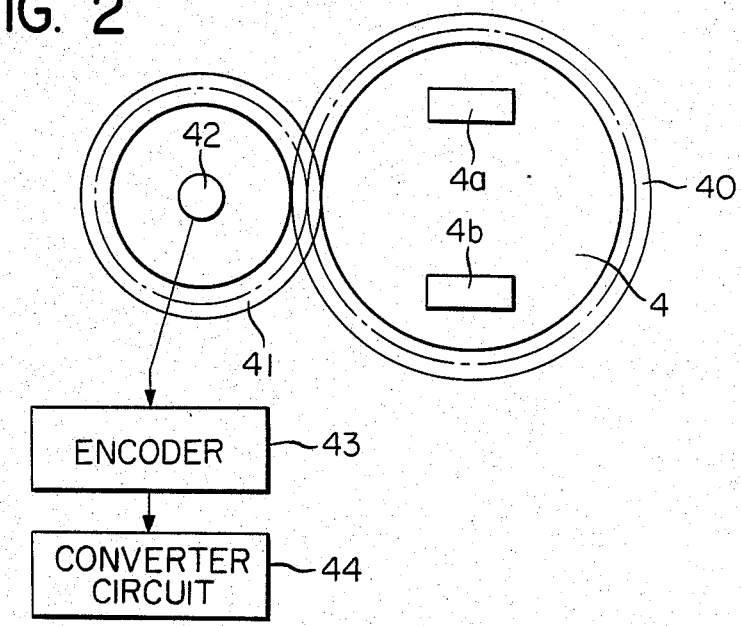
FIG. 2 shows a first diaphragm, a device for rotating it and a device for displaying the direction of the astigmatism main diametral line.
Figure 3:
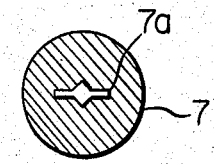
FIG. 3 is a plan view of a second diaphragm.
Figure 6:
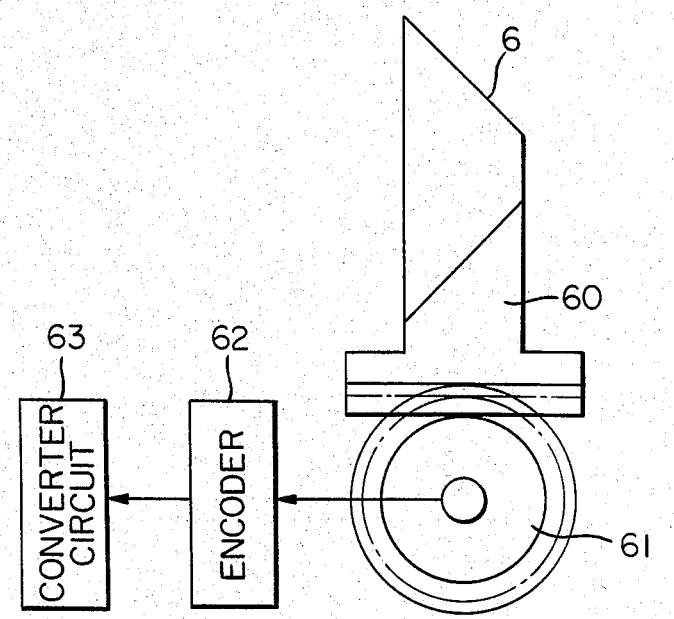
FIG. 6 shows a moving device for a focusing prism and a device for displaying the refractive power.

In the reflection optical axis of an obliquely disposed half-mirror 1 (the reflection optical axis being part of the optical path), there are provided, at successive positions along the optical path, a first imaging lens 2, a reflecting mirror 3, a first diaphragm 4 having a pair of openings 4a and 4b (FIG. 2) formed symmetrically with the optical path, a second imaging lens 5, a focusing prism 6, a second diaphragm 7 formed with a quasi-rectangular opening 7a (FIG. 3) having a protruding central portion, and a light source 8. The first imaging lens 2 renders a predetermined position at one side of lens 2 (the cornea of the examinee's eye is set at this position) conjugate with the first diaphragm 4 at the opposite side by alignment. The first diaphragm 4, as shown in FIG. 2, is rotatable about the optical axis by rotating a rotatable knob 42 having a gear 41 meshing with a gear 40 formed on the outer periphery of the first diaphragm. The amount of rotation of the knob 42 is read by an angle reading device, for example, a position encoder or a potentiometer. In FIG. 2, a rotary encoder 43 having a rotatable disc secured to the knob 42 is provided and the angle read by this encoder 43 is applied as input to a converter circuit 44 for converting said angle into a degree of astigmatism, whereby the degree of astigmatism is displayed. Also the focusing prism 6, as shown in FIG. 6, is movable to change the length of the optical path between diaphragm 4 and 7 (as indicated by the arrow in FIG. 1) by rotation of a pinion 61 meshing with a rack member 60 integral with the focusing prism 6, and by the movement of the focusing prism 6, the effective position of the second diaphragm 7 relative to the first diaphragm 4 can be varied. The amount of movement of the focusing prism 6 is displayed by converting the output of a rotary encoder 62 coupled to the pinion 61 into a frequency. The opening 7a formed in the second diaphragm 7 is such as shown in FIG. 3, for example, and the optical path is so disposed as to pass through the center of the opening 7a, and the second diaphragm 7 is rotatable about the optical path by a rotating mechanism similar to the diaphragm 4 shown in FIG. 2.

A main body 10 holding the above-described optical system is disposed for three-dimensional movement on a base 11 by means of a well-known mechanism, for example, a stand 12 used in a slit lamp microscope or an eye fundus camera well known as an ophthalmologic instrument, and a fixing pedestal 13 for fixing the examinee's head thereon is secured to the base 11. Alignment between the examinee's eye $E_1$ fixed to the fixing pedestal 13 and the main body 10 is carried out so that the diaphragm 4 becomes conjugate with the cornea of the examinee's eye $E_1$. Various means therefor are conceivable, and for example, the design may be such that the intensity of the light source 8 is increased and the stand 12 is moved until the examiner who observes the examinee's eye $E_1$ through the half-mirror 1 confirms that the image of the diaphragm 4 is formed on the surface of the cornea of the examinee's eye $E_1$. Of course, focusing may be effected by movement of the first imaging lens 2 in the direction of the optical axis. However, where the stand 12 is one as described above, the first imaging lens 2 may be stationary. If the first imaging lens 2 is stationary, the main body 10 of the apparatus can be moved in the base 11 so that the cornea of the examinee's eye $E_1$ comes to a position conjugate with the first diaphragm 4 by the first imaging lens 2.

Figure 4A:
FIG. 4A shows a usually observed image of an examinee having an astigmatic eye.

In such a condition, when the examinee having an astigmatic eye is looking forward through the half-mirror 1, the image is shown in FIG. 4A, is observed by the examinee. (The portion indicated by hatching is light.)

This case is a condition in which the direction of the astigmatism axis of the examinee's eye $E_1$ is not coincident with the direction of the opening in the diaphragm 4, namely, the most usual condition.

Figure 4B:
FIG. 4B shows the image when two images are partially coincident with each other.

Therefore, the pinion 61 is first rotated to move the focusing prism 6 to change the length of the optical path between diaphragms 4 and 7. When the two images become partially coincident with each other as shown in FIG. 4B, the focusing prism is moved until the examinee responds. At that time, the amount of movement of the prism 6 corresponds to the refractive power of the examinee's eye $E_1$. The refractive power is displayed by the converter circuit 63.

Figure 4C:
FIG. 4C shows the image when two images are completely coincident with each other.

Subsequently, the diaphragm 4 and the diaphragm 7 are rotated and, when the two images become completely coincident with each other, the focusing prism is moved until the examinee responds (FIG. 4C). The then angle of rotation of the diaphragm 4 corresponds to the direction of the astigmatism main diametral line of the examinee's eye $E_1$. The direction of the astigmatism main diametral line is displayed by the converter circuit 44.

Accordingly, through the above-described operation, the direction of one astigmatism main diametral line in the astigmatic eye $E_1$ and the refractive power of the eye in this direction can be known.

Subsequently, the diaphragm 4 and the diaphragm 7 are further rotated by 90° and thereafter, if the focusing prism 6 is moved until the examinee responds when the two images become coincident with each other, the refractive power of the eye for the direction of the other astigmatism main diametral line can be known from the then position of the focusing prism 6. This value is also displayed in a manner similar to what has been described above.

Figure 4D:
FIG. 4D shows the image when the direction of the diaphragm opening is coincident with the direction of one astigmatism main diametral line of the examinee.

If the direction of the opening in the diaphragm 4 is coincident with the direction of one astigmatism main diametral line of the examinee's eye $E_1$, the examiner can observe the image as shown in FIG. 4D and therefore, in this case, the coincident image as shown in FIG. 4C can be made visible merely by moving the focusing prism 6.

It will be seen that the movement of the focusing prism 6 may take place earlier than the rotation of the diaphragms 4 and 7 or the latter may take place earlier than the former, but it is very difficult to judge, by rotating the diaphragms 4 and 7 that the two images in the condition of FIG. 4A have been vertically arranged as shown in FIG. 4D, and therefore, it is preferable to design the apparatus such that the focusing prism 6 is first moved and then the diaphragms 4 and 7 are rotated.

Where the examinee's eye $E_1$ is not an astigmatic eye, irrespective of the angle of rotation of the first diaphragm 4, the image of the diaphragm is never seen skewed as shown in FIG. 4A. Also, when the initial position of the focusing prism 6 lies at a position corresponding to zero diopter, the image of the diaphragm will always be seen spaced apart by an amount corresponding to the frequency thereof as shown in FIG. 4D.

Figure 5:
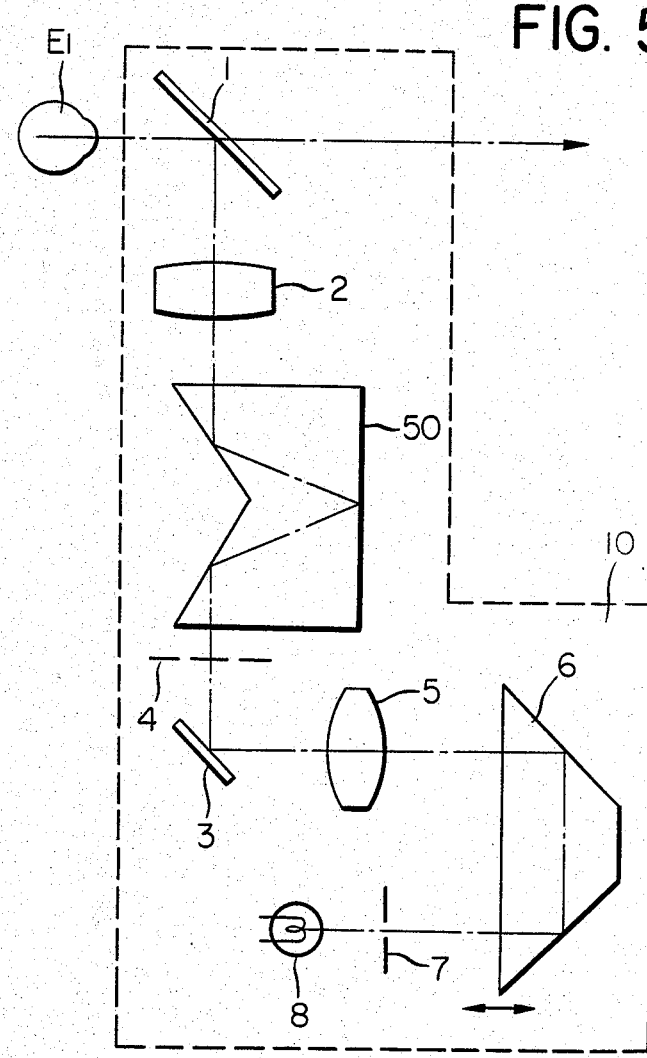
FIG. 5 shows an example in which an optical device for rotating a diaphragm 4 and a diaphragm 7 in synchronism with each other is added to the arrangement of FIG. 1.

In the foregoing description, the diaphragm 4 and the diaphragm 7 have been described as being rotated in synchronism with each other. Although the mechanisms therefor may be coupled together so that the diaphragms 4 and 7 are rotated in synchronism with each other by transmitting the rotation of the shaft 42 of FIG. 2 through an intermediate gear or the like, it is preferable to use optical processing. That is, if, as shown in FIG. 5, an image rotating prism 50 is inserted between the objective lens 2 and the diaphragm 4 and rotation of this prism 50 is utilized, the construction will become simpler.

The opening in diaphragm 7 forms a "mark" that is projected onto the eye to be examined. In the form shown, the mark is generally rectangular with a portion central to the length that is expanded in the direction of the width. The shapes of the openings in the diaphragms 4 and 7 are not restricted to the shown shapes, but may be other shapes, for example, circular shape, and the diaphragm 7 and the light source 8 may be replaced by marks which themselves emit light.

Further, the diaphragm 4 and the diaphragm 7 need not rotate together with each other, but at least the diaphragm 4 alone should rotate. The focusing prism 6 need not always be used to change the position of the diaphragm 7 relative to th diaphragm 4, but the diaphragm 7 may be made movable along the optical path. Still further, a wedge-shaped prism may be made insertable between the diaphragm 4 and the diaphragm 7 to vary the length of the optical path.

The half-mirror 1 may be one through which the examinee can see a long distance, whereby the examinee's eye is in relaxed condition and can see the image of the diaphragm 7 overlapped with a distant image.

I claim:

1. An apparatus for subjectively measuring the refractive power of an eye, said apparatus comprising an optical system having an optical path and including:
   (a) diaphragm means at a first position along said optical path and having a pair of openings;
   (b) mark means at a second position along said optical path and having a mark to be observed by the eye;
   (c) first imaging lens means at a third position along said optical path for causing a fourth position along said optical path, at which said eye is to be disposed, to be conjugate with said first position and for forming an image of said openings at said fourth position;
   (d) second imaging lens means at a fifth position along said optical path for forming an image of said mark through said openings and said first imaging lens means;
   (e) means for varying the length of the optical path between said mark means and said diaphragm means so that said image of said mark may be formed on the fundus of the eye; and
   (f) means for converting the optical path length between said diaphragm means and said mark means into the refractive power of the eye.

2. An apparatus for subjectively measuring the refractive power of an eye, said apparatus comprising an optical system having an optical path and including:

(a) diaphragm means at a first position along said optical path and having a pair of openings;

(b) mark means at a second position along said optical path and having a mark to be observed by the eye;

(c) first imaging lens means at a third position along said optical path for causing a fourth position along said optical path, at which said eye is to be disposed, to be with said first position and for forming an image of said openings at said fourth position;

(d) second imaging lens means at a fifth position along said optical path for forming an image of said mark through said openings and said first imaging lens means;

(e) means for varying the length of the optical path between said mark means and said diaphragm means so that said image of said mark may be formed on the fundus of the eye;

(f) rotating means for rotating said image of said openings about said optical path;

(g) first converter means for converting the angle of rotation of said rotating means into the direction of an astigmatism axis of the eye; and (h) second converter means for converting the optical path length between said diaphragm means and said mark means into the refractive power of the eye.

3. An apparatus according to claim 2, wherein the openings of said pair are symmetric with respect to said optical path.

4. An apparatus according to claim 2, further including beam splitter means disposed across the optical path between said third and fourth positions.

5. An apparatus according to claim 2, wherein said varying means has prism means provided between said diaphragm means and said mark means for bending said optical path by 180°, and moving means for moving said prism means to change the length of said optical path.

6. An apparatus according to claim 5, wherein said second converter means includes an encoder device coupled to said moving means and putting out a signal corresponding to the position of said prism means, and a converter device for converting the output signal of said encoder device to the refractive power.

7. An apparatus according to claim 2, wherein said rotating means has a gear device for rotating said diaphragm means about said optical path.

8. An apparatus according to claim 7, wherein said first converter means includes a rotary encoder coupled to said gear device and putting out an angle signal corresponding to the angle of rotation of said diaphragm means.

9. An apparatus according to claim 2, wherein said rotating means has an image rotating prism provided between said first imaging lens means and said diaphragm means.

10. An apparatus according to claim 2, wherein said mark means has a generally rectangular mark with a portion central to the length of the mark that is expanded in the direction of the width of the mark.

11. An apparatus according to claim 2, wherein said mark means has a mark plate with an opening substantially centrally thereof, and a light source disposed behind said mark plate.

12. An apparatus for subjectively measuring the refractive power of an eye, said apparatus comprising an optical system having an optical path and including:

(a) beam splitter means disposed along said optical path for splitting said optical path into a first part that is reflected from the beam splitter means and a second part that is transmitted by the beam splitter means;

(b) diaphragm means provided on the first part of the optical path and having a pair of openings symmetric with the first part of the optical path;

(c) positive lens means provided along the first part of the optical path between said eye and said diaphragm means to cause the diaphragm means and the surface of the eye to be conjugate with each other; and (d) projection means along said first part of the optical path for projecting onto said eye through said openings a mark to be observed by said eye, said projection means having optical means for causing said mark to be conjugate with the fundus of the eye.

13. An apparatus according to claim 12, wherein said projection means includes lens means for forming an image of the mark on the eye through said openings.

* * * * *